United States Patent
Kajiyama et al.

(10) Patent No.: US 12,115,020 B2
(45) Date of Patent: Oct. 15, 2024

(54) TWO-DIMENSIONAL ARRAY ULTRASONIC PROBE AND ADDITION CIRCUIT

(71) Applicant: HITACHI, LTD., Tokyo (JP)

(72) Inventors: Shinya Kajiyama, Tokyo (JP); Yoshihiro Hayashi, Tokyo (JP); Tadahiro Nabeta, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 674 days.

(21) Appl. No.: 17/229,916

(22) Filed: Apr. 14, 2021

(65) Prior Publication Data
US 2021/0386401 A1 Dec. 16, 2021

(30) Foreign Application Priority Data
Jun. 16, 2020 (JP) ................................. 2020-103537

(51) Int. Cl.
*A61B 8/00* (2006.01)
*A61B 8/14* (2006.01)
(Continued)

(52) U.S. Cl.
CPC .......... *A61B 8/4494* (2013.01); *A61B 8/4444* (2013.01); *B06B 1/0207* (2013.01);
(Continued)

(58) Field of Classification Search
None
See application file for complete search history.

(56) References Cited

U.S. PATENT DOCUMENTS 4,317,369 A * 3/1982 Johnson ................. A61B 8/406
73/607
4,486,867 A * 12/1984 Hill .......................... G01S 7/52
367/87
(Continued)

FOREIGN PATENT DOCUMENTS

CN 102138807 A 8/2011
CN 103767732 A 5/2014
(Continued)

OTHER PUBLICATIONS

1 Chinese Office Action received in corresponding Chinese Application No. 202110403127.8 mailed Jun. 29, 2023.

*Primary Examiner* — Isam A Alsomiri
*Assistant Examiner* — Jonathan D Armstrong
(74) *Attorney, Agent, or Firm* — MATTINGLY & MALUR, PC

(57) ABSTRACT

Provided are a two-dimensional array ultrasonic probe and an addition circuit that switch an addition unit of a reception signal according to a reception channel of a main unit while preventing an increase in a chip area. The addition circuit includes, between addition output terminals that output an addition signal and transducer channels, wirings provided for each transducer channel row including the transducer channels arranged in a vertical direction on a subarray basis and coupled to the transducer channels of the corresponding transducer channel row, output switches provided for each of the wirings and coupled to the corresponding transducer channel row wiring, and an inter-output switch that couples wirings corresponding to transducer channel rows adjacent in the horizontal direction via the output switches.

16 Claims, 15 Drawing Sheets

(51) Int. Cl.
  *B06B 1/02* (2006.01)
  *G01S 15/89* (2006.01)
(52) U.S. Cl.
  CPC ...... *G01S 15/8925* (2013.01); *G01S 15/8927* (2013.01); *G01S 15/8993* (2013.01); *A61B 8/145* (2013.01); *B06B 2201/76* (2013.01)

(56) References Cited

U.S. PATENT DOCUMENTS

| | | | | |
|---|---|---|---|---|
| 4,852,577 | A * | 8/1989 | Smith | A61B 8/0858 600/443 |
| 5,271,403 | A * | 12/1993 | Paulos | A61B 8/0866 600/443 |
| 5,460,180 | A * | 10/1995 | Klepper | B06B 1/0622 600/447 |
| 5,517,995 | A * | 5/1996 | Klepper | G01S 15/8927 600/447 |
| 5,636,147 | A * | 6/1997 | Tolmie | B06B 1/0207 703/5 |
| 5,675,341 | A * | 10/1997 | Vallancourt | H03M 1/366 341/158 |
| 6,192,760 | B1 | 2/2001 | MacLauchlan et al. | |
| 6,238,346 | B1 * | 5/2001 | Mason | G01S 15/8927 600/459 |
| 7,139,532 | B2 * | 11/2006 | Veillette | G01S 7/52025 455/87 |
| 9,983,176 | B2 | 5/2018 | Savord | |
| 9,986,976 | B2 * | 6/2018 | Kremsl | G01S 7/5208 |
| 10,806,431 | B2 * | 10/2020 | Chen | G01S 15/8925 |
| 2003/0149363 | A1 * | 8/2003 | Dreschel | B06B 1/00 600/437 |
| 2011/0148678 | A1 * | 6/2011 | Hu | H03M 1/0668 341/150 |
| 2012/0059265 | A1 * | 3/2012 | Franchini | H03F 1/083 600/459 |
| 2012/0326901 | A1 * | 12/2012 | Zhao | H03M 1/06 341/172 |
| 2015/0087991 | A1 * | 3/2015 | Chen | G01S 7/52025 330/253 |
| 2015/0319379 | A1 * | 11/2015 | Nussmeier | G01J 5/22 348/165 |
| 2016/0183927 | A1 * | 6/2016 | Kremsl | G01S 7/5208 600/443 |
| 2017/0290568 | A1 * | 10/2017 | Ko | A61B 8/4272 |
| 2018/0263594 | A1 * | 9/2018 | Morimoto | H01L 29/786 |
| 2019/0187278 | A1 * | 6/2019 | Ozawa | G10K 11/02 |

FOREIGN PATENT DOCUMENTS

| | | |
|---|---|---|
| CN | 104471437 A | 3/2015 |
| CN | 108405291 A | 8/2018 |
| JP | 07-113794 A | 5/1995 |
| JP | 09-75349 A | 3/1997 |
| JP | 2000-185037 A | 7/2000 |
| JP | 6165855 B2 | 7/2017 |
| WO | 2017/47329 A1 | 3/2017 |

* cited by examiner

FIG. 11

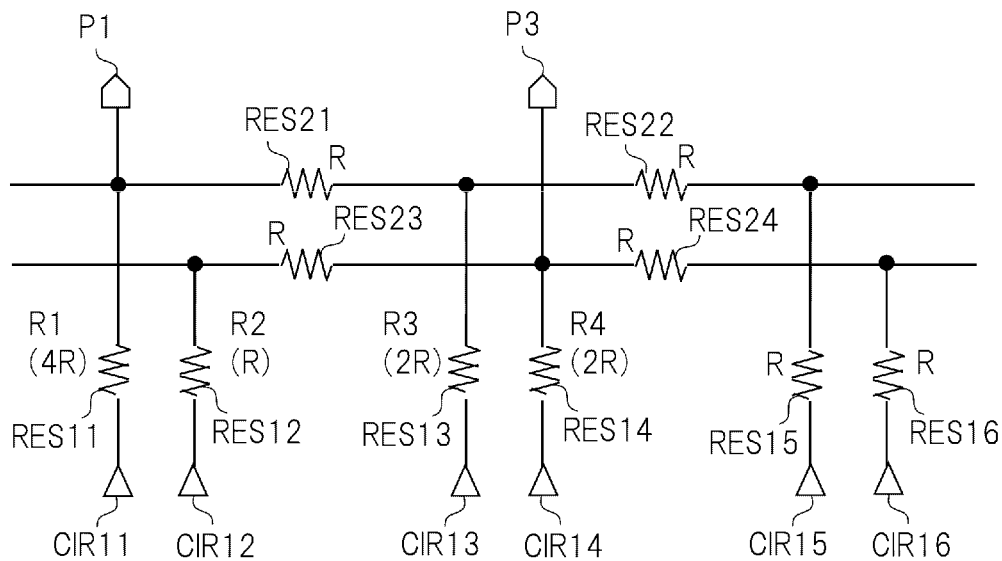

FIG. 12

$$A11 = \frac{R + (2R//R3)}{R1 + R + (2R//R3)} \quad \cdots \text{FORMULA 1}$$

$$A13 = \frac{2R}{R3 + 2R} \cdot \frac{R1}{(2R//R3) + R + R1} \quad \cdots \text{FORMULA 2}$$

$$A15 = \frac{R3}{2R + R3} \cdot \frac{R1}{(2R//R3) + R + R1} \quad \cdots \text{FORMULA 3}$$

$$A12 = \frac{2R//R4}{R2 + R + (2R//R4)} \quad \cdots \text{FORMULA 4}$$

$$A14 = \frac{2R//(R + R2)}{2R//(R + R2) + R4} \quad \cdots \text{FORMULA 5}$$

$$A16 = \frac{(R + R2)//R4}{(R + R2)//R4 + 2R} \quad \cdots \text{FORMULA 6}$$

TWO-DIMENSIONAL ARRAY ULTRASONIC PROBE AND ADDITION CIRCUIT

CROSS-REFERENCE TO RELATED APPLICATION

The present application claims priority from Japanese application JP2020-103537, filed on Jun. 16, 2020, the contents of which is hereby incorporated by reference into this application.

BACKGROUND OF THE INVENTION

1. Field of the Invention

The present invention relates to a two-dimensional array ultrasonic probe and an addition circuit.

2. Description of the Related Art

An ultrasonic diagnostic apparatus is a medical diagnostic apparatus which is non-invasive to a human body and has high safety. The ultrasonic diagnostic apparatus can display, for example, heart pulsation and fetal movement in real time by bringing an ultrasonic probe into contact with a body surface.

In recent years, an ultrasonic diagnostic apparatus capable of obtaining a three-dimensional stereoscopic image has been developed. In order to acquire the three-dimensional stereoscopic image, it is necessary to change transducers in the ultrasonic probe from a one-dimensional array in the related art to a two-dimensional array. In this case, the number of transducers increases by the square compared to the ultrasonic probe in the related art, and thus a configuration of the apparatus including a wiring and the like becomes complicated.

Since it is impossible to increase the number of cables coupling the ultrasonic probe and a main unit by the square, it is necessary to reduce the number of reception signals by performing phasing addition in the ultrasonic probe. In order to implement the phasing addition in the ultrasonic probe, for example, a transmission and reception function and a phasing addition function are implemented as an IC, and a transmission and reception circuit is arranged for each transducer in the IC.

Specifically, in the two-dimensional array ultrasonic probe, several to ten thousand or more transmission and reception circuits may be mounted on the IC. Depending on the number of reception channels of the main unit of the ultrasonic diagnostic apparatus, an addition circuit of the IC may reduce several to ten thousand or more reception signals to about 200 channels by the phasing addition.

FIG. 16 is a diagram showing an example of a method for adding the reception signals in the two-dimensional transducer array. FIG. 16 shows a two-dimensional transducer channel array ARRAY having 24×12=288 transducer channels. In FIG. 16, the 288 transducer channels are divided into 72 sub arrays SUB each having 2×2=4 transducer channels as one unit. Then, by transmitting an addition signal obtained by adding the reception signals of the transducer channels on a sub array basis to the main unit, it is possible to reduce 288 channels to 72 channels which is ¼ thereof, and to couple the ultrasonic probe to the main unit with 72 cables.

However, when the ultrasonic probe having the configuration in FIG. 16 is coupled to the main unit having less than 72 reception channels, signals of a part of the transducer channels cannot be used. Therefore, in the main unit having a small number of reception channels, a signal-to-noise ratio deteriorates.

FIG. 17 is a diagram showing another example of the method for adding the reception signals in the two-dimensional transducer array. In FIG. 17, 288 transducer channels are divided into 32 subarrays (203) each having 3×3=9 transducer channels as one unit. As described above, the number of channels can be reduced by increasing the number of transducer channels included in the sub array.

As described above, if an addition unit of the transducer channels in the IC mounted on the two-dimensional array ultrasonic probe can be switched in accordance with the number of reception channels of the coupled main unit, a wide reception aperture can be used regardless of the number of reception channels of the main unit, and the signal-to-noise ratio can be ensured even in the main unit having a small number of reception channels.

Japanese Patent No. 6165855 (PTL 1), for example, discloses a method for switching the addition unit of the transducer channels. PTL 1 discloses switching coupling between a transducer channel and a main unit reception channel using a controllable switch.

FIG. 18 is obtained by redrawing FIG. 4 in PTL 1 from a viewpoint of the inventor. A matrix switch in FIG. 18 enables a two-dimensional array ultrasonic probe to be used with a probe cable that is cost-effective for main unites having different numbers of reception channels. In FIG. 18, a reception circuit (Rx) of each transducer channel can be coupled to all reception channels of a main unit via a switch (SW).

In this case, when the number of transducer channels of the two-dimensional array ultrasonic probe is N and a maximum number of reception channels of the main unit is M, N×M switches are necessary for the IC. In addition, M wirings are provided on a transmission and reception circuit of one transducer channel.

However, the number of transducer channels used in the two-dimensional array ultrasonic probe may be several to ten thousand or more, and the maximum number of reception channels of the main unit may be about 200. In this case, since a large number of switches and a large number of wirings are provided, a chip area of the addition circuit increases.

SUMMARY OF THE INVENTION

Accordingly, an object of the invention is to provide a two-dimensional array ultrasonic probe capable of switching an addition unit of a reception signal according to a reception channel of a main unit while preventing an increase in a chip area.

In the inventions disclosed in the application, an outline of typical ones will be briefly described as follows.

In a two-dimensional array ultrasonic probe according to a representative embodiment of the invention, a plurality of transducer channels are arranged in a first direction and a second direction. Each of the plurality of transducer channels including an ultrasonic transducer and a reception circuit that transmits a reception signal of the ultrasonic transducer. The plurality of transducer channels are divided into a plurality of subarrays on a basis of an addition unit of the reception signal. The two-dimensional array ultrasonic probe includes, an addition circuit that generates an addition signal by adding reception signals of the transducer channels included in the subarrays on a subarray basis. The addition circuit includes, between an addition output terminal that outputs the addition signal and the transducer channels, a transducer channel row wiring provided for each transducer channel row including the transducer channels arranged in the first direction on a subarray basis and coupled to the transducer channels of the corresponding transducer channel row, a first switch provided for each transducer channel row wiring and coupled to the corresponding transducer channel row wiring, and a second switch that couples transducer channel row wirings corresponding to transducer channel rows adjacent in the second direction via the first switch.

Effects obtained by typical ones of the inventions disclosed in the present application will be briefly described as follows.

That is, according to representative embodiments of the invention, it is possible to switch the addition unit of the reception signal in accordance with the reception channel of the main unit while preventing an increase in the chip area.

BRIEF DESCRIPTION OF THE DRAWINGS

FIG. 11 is a diagram showing an equivalent circuit of FIG. 10.

FIG. 12 is a diagram showing a list of formulas of a signal attenuation rate in FIG. 11.

DESCRIPTION OF THE PREFERRED EMBODIMENTS

Figure 1:
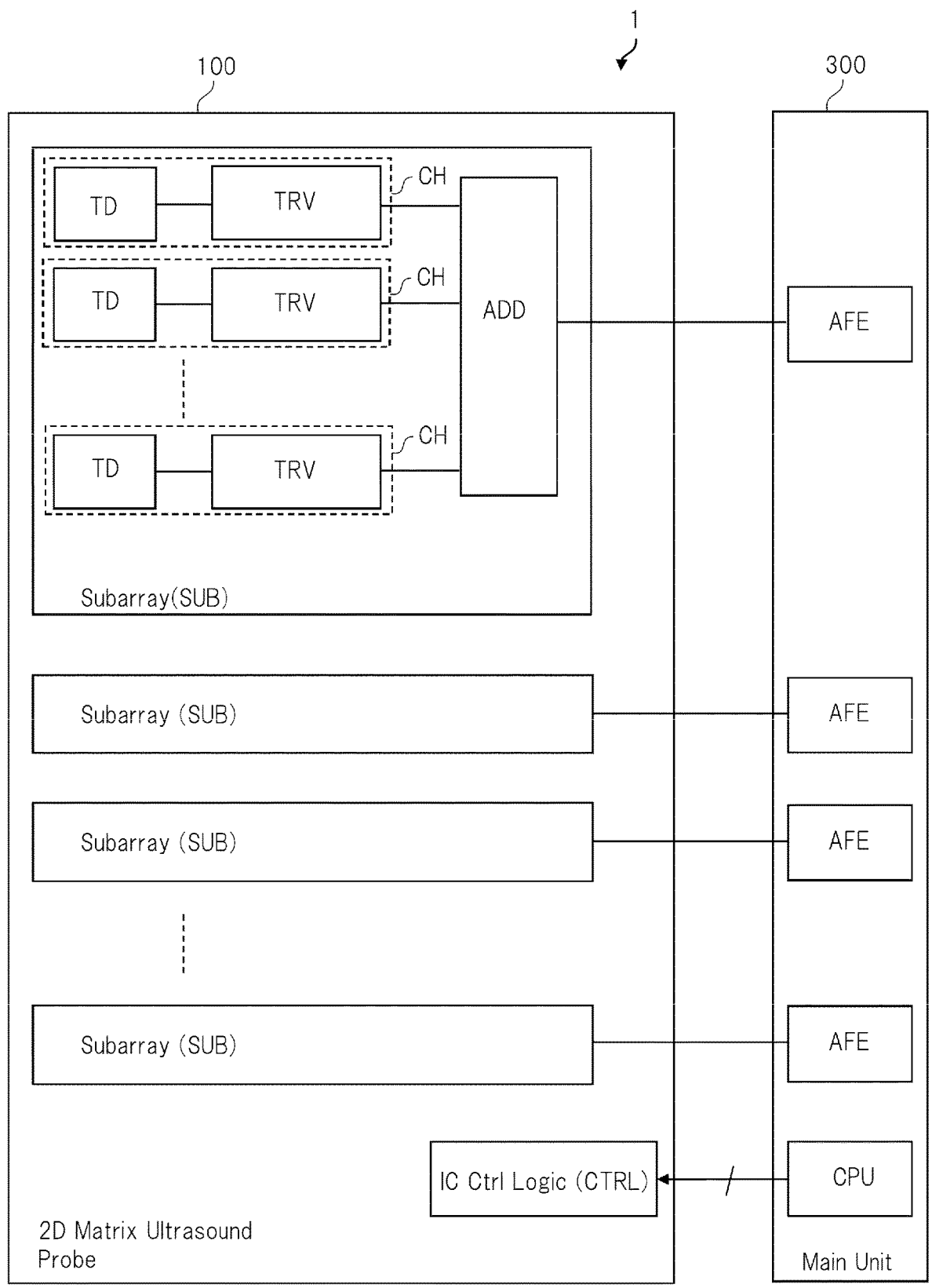
FIG. 1 is a diagram showing an example of a configuration of an ultrasonic diagnostic apparatus including a two-dimensional array ultrasonic probe according to a first embodiment of the invention.

Embodiments of the invention will be described below with reference to the drawings. Each of the embodiments described below is an example for implementing the invention, and does not limit the technical scope of the invention. In the embodiments, members having the same function are designated by the same reference numeral, and repeated description thereof will be omitted unless particularly necessary.

First Embodiment

<Configuration of Ultrasonic Diagnostic Apparatus>

FIG. 1 is a diagram showing an example of a configuration of an ultrasonic diagnostic apparatus including a two-dimensional array ultrasonic probe according to a first embodiment of the invention. As shown in FIG. 1, an ultrasonic diagnostic apparatus 1 includes a two-dimensional array ultrasonic probe 100 and a main unit 300. The ultrasonic diagnostic apparatus 1 generates a three-dimensional stereoscopic image of an inspection object in the main unit 300 based on a signal transmitted from the two-dimensional array ultrasonic probe 100.

<Main Unit>

The main unit 300 includes a processor CPU, a plurality of reception channels (analog front ends) AFE, and the like.

The processor CPU transmits a control signal to a control logic circuit IC in the two-dimensional array ultrasonic probe 100. The two-dimensional array ultrasonic probe 100 is controlled based on the control signal. The control signal includes, for example, switching between transmission and reception, beam forming of an ultrasonic wave, and delay control for beam scanning. Although not particularly limited, when a transmission circuit is not a linear amplifier system but a pulser system, a waveform is transmitted to a pulser as a digital value. Therefore, the control logic circuit IC may include a waveform memory that stores waveform data transmitted by the pulser.

An addition signal obtained by adding a reception signal in a subarray (described in detail later) of the two-dimensional array ultrasonic probe 100 is transmitted to a corresponding reception channel AFE. Based on the transmitted addition signal, for example, the processor CPU performs signal processing.

<Two-Dimensional Array Ultrasonic Probe>

Figure 17:
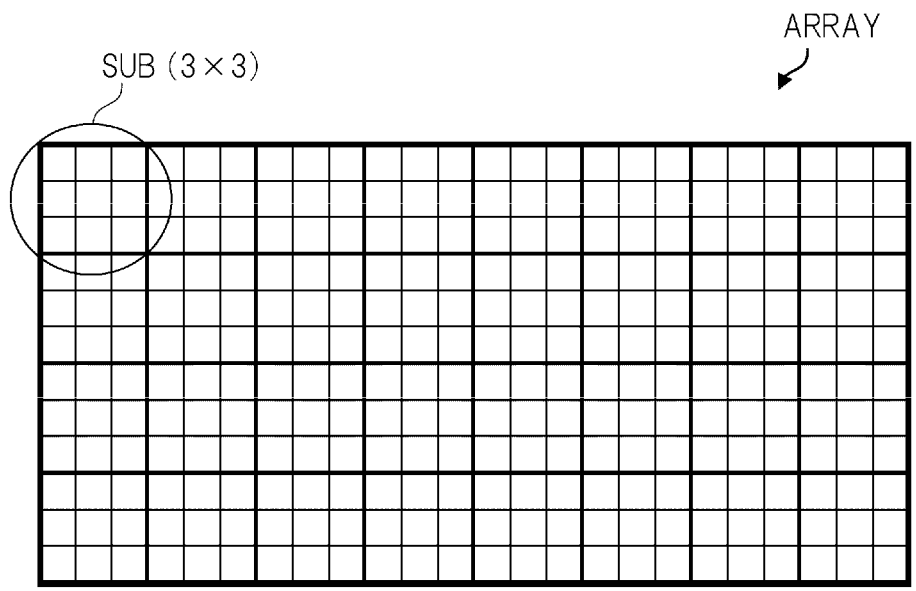
FIG. 17 is a diagram showing another example of the method for adding a reception signal in a two-dimensional transducer array.
Figure 18:
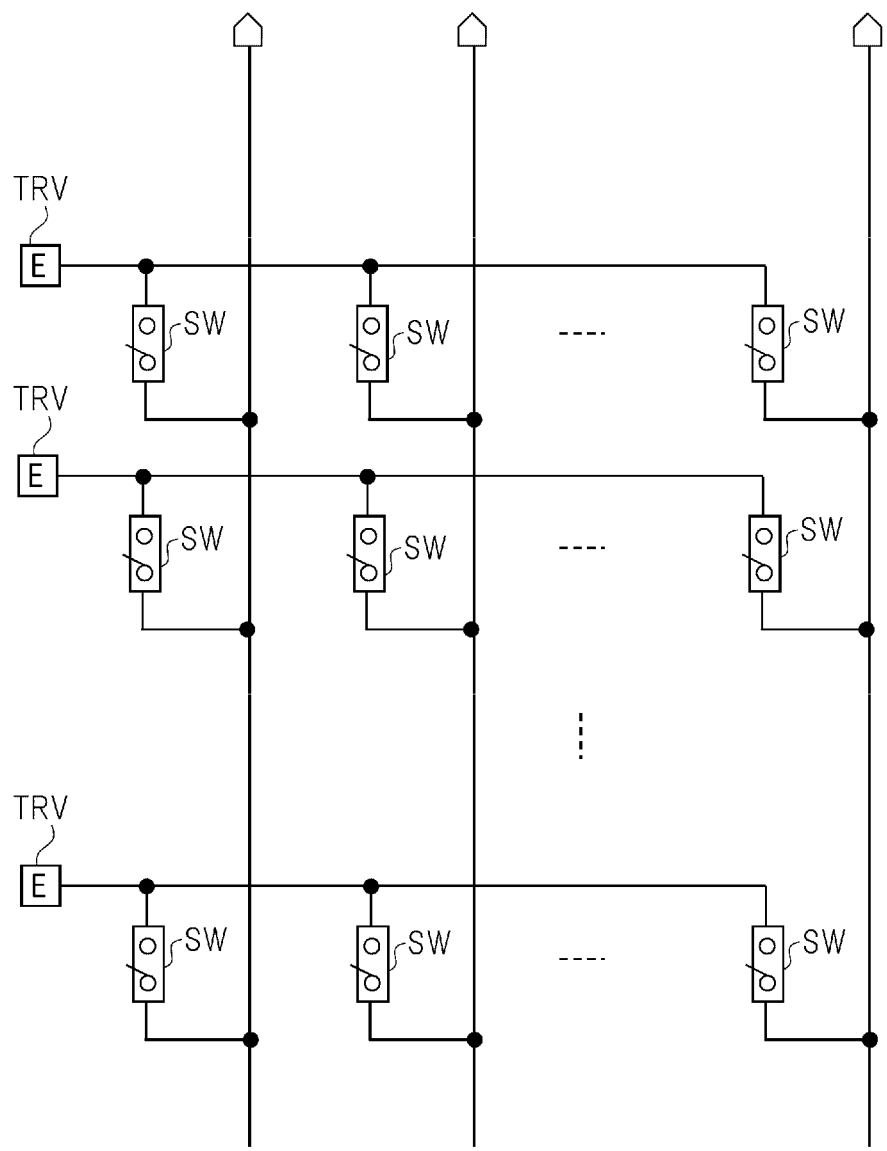
FIG. 18 is a diagram obtained by redrawing FIG. 4 in PTL 1 from a viewpoint of the inventor.

In the two-dimensional array ultrasonic probe 100 in FIG. 1, for example, as described with reference to FIGS. 1 and 17, a plurality of transducer channels CH are arranged in a two-dimensional array. As shown in FIG. 1, the two-dimensional array ultrasonic probe 100 is provided with a plurality of subarrays SUB including the plurality of transducer channels CH. The subarrays SUB respectively correspond to the plurality of reception channel AFEs included in the main unit 300.

The transducer channels CH arranged in an array are divided into a plurality of subarrays SUB. Division of the transducer channels CH is performed such that each subarray SUB includes the same number of transducer channels CH as one another, for example. The subarray SUB is coupled to an addition circuit ADD.

As shown in FIG. 1, each transducer channel CH includes an ultrasonic transducer TD and a transmission and reception circuit TRV. The ultrasonic transducer TD is coupled to the corresponding transmission and reception circuit TRV. That is, the ultrasonic transducer TD and the transmission and reception circuit TRV are coupled to each other on a one-to-one basis. The ultrasonic transducer TD may be included in the transmission and reception circuit TRV. In this case, the ultrasonic transducer TD and the transmission and reception circuit TRV may be collectively referred to as the transmission and reception circuit TRV.

The ultrasonic transducer TD transmits the ultrasonic wave by performing vibration by a drive signal supplied from the corresponding transmission and reception circuit TRV. At this time, a predetermined delay is given to the drive signal supplied to each ultrasonic transducer TD. Accordingly, a plurality of ultrasonic transducers TD are caused to cooperate with one another to perform the beam forming and the beam scanning of the ultrasonic wave to an inspection object.

The ultrasonic wave subjected to the beam forming is reflected by the inspection object. The ultrasonic transducer TD receives a weak reflection signal (ultrasonic wave) from the inspection object. The ultrasonic transducer TD receives the weak reflection signal from the inspection object and vibrates, thereby converting the reflection signal into an electric signal. The electric signal corresponding to the reflection signal is transmitted to the transmission and reception circuit TRV as a reception signal of the ultrasonic transducer TD.

Figure 2:
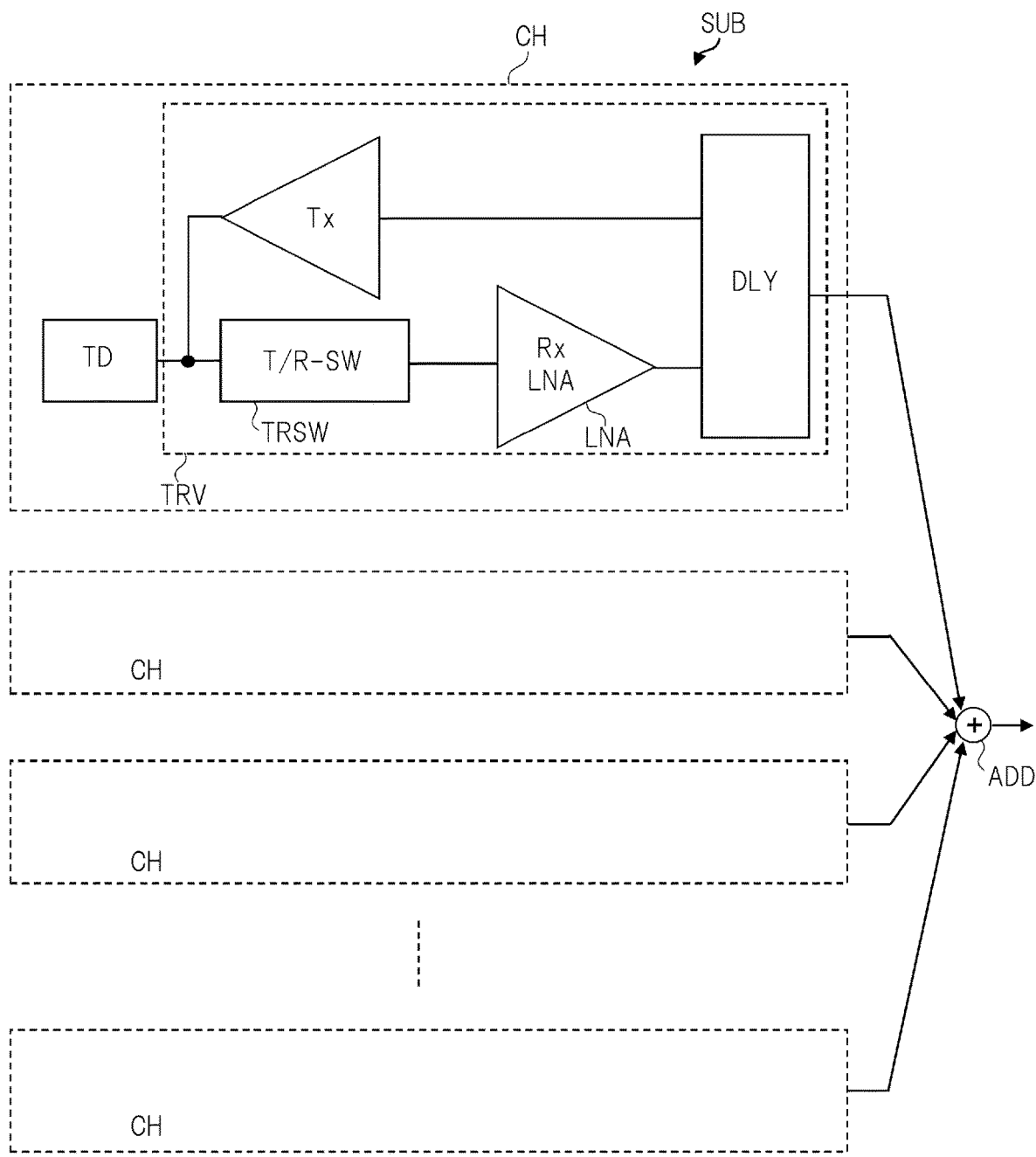
FIG. 2 is a circuit block diagram showing an example of a configuration of a transmission and reception circuit.

FIG. 2 is a circuit block diagram showing an example of a configuration of a transmission and reception circuit. FIG. 2 shows a specific configuration of the transmission and reception circuit TRV while showing a configuration of the subarray SUB. The transmission and reception circuit TRV includes a transmission circuit Tx, a transmission and reception separation switch TRSW, a low noise amplifier LNA, and a delay circuit DLY.

The transmission circuit Tx has an input side coupled to the delay circuit DLY, and an output side coupled to the ultrasonic transducer TD and the transmission and reception separation switch TRSW. The transmission circuit Tx includes, for example, a high breakdown voltage element (for example, a MOSFET). The transmission circuit Tx generates a high-voltage drive signal based on the drive signal transmitted from the delay circuit DLY, and transmits the drive signal to the ultrasonic transducer TD. The ultrasonic transducer TD transmits the ultrasonic wave by vibration based on the high-voltage drive signal.

The transmission and reception separation switch TRSW is constituted by a high breakdown voltage element for receiving the high-voltage drive signal. When the drive signal is transmitted from the transmission circuit Tx, the transmission and reception separation switch TRSW is turned off to protect the reception circuit from the high-voltage drive signal. Further, when the reception signal is transmitted from the ultrasonic transducer TD, the transmission and reception separation switch TRSW is turned on to transmit a minute reception signal to the low noise amplifier LNA. The low noise amplifier LNA is a low noise circuit that amplifies the reception signal. The low noise amplifier LNA transmits the amplified reception signal to the delay circuit DLY. Hereinafter, the amplified reception signal may be referred to as the reception signal.

The delay circuit DLY gives the predetermined delay to the drive signal to be transmitted to the transmission circuit Tx. Delay time in each delay circuit DLY is set to a predetermined value. Then, by giving the predetermined delay to the drive signal in a plurality of delay circuits DLY, the beam forming and the beam scanning of the ultrasonic wave are performed.

Each delay circuit DLY delays the amplified reception signal transmitted from the low noise amplifier LNA. Accordingly, phasing of the reception signal is performed among the plurality of transducer channels CH. The reception signal subjected to phasing is transmitted to the addition circuit. In the following description, the phased reception signal may be referred to as the reception signal.

<Addition Circuit>

Next, the addition circuit ADD will be described in detail. The addition circuit ADD is a circuit that generates the addition signal by adding the signal output from each of the transducer channels CH included in the subarray SUB, and transmits the addition signal from an addition output terminal OUT to a corresponding reception channel AFE.

Figure 3:
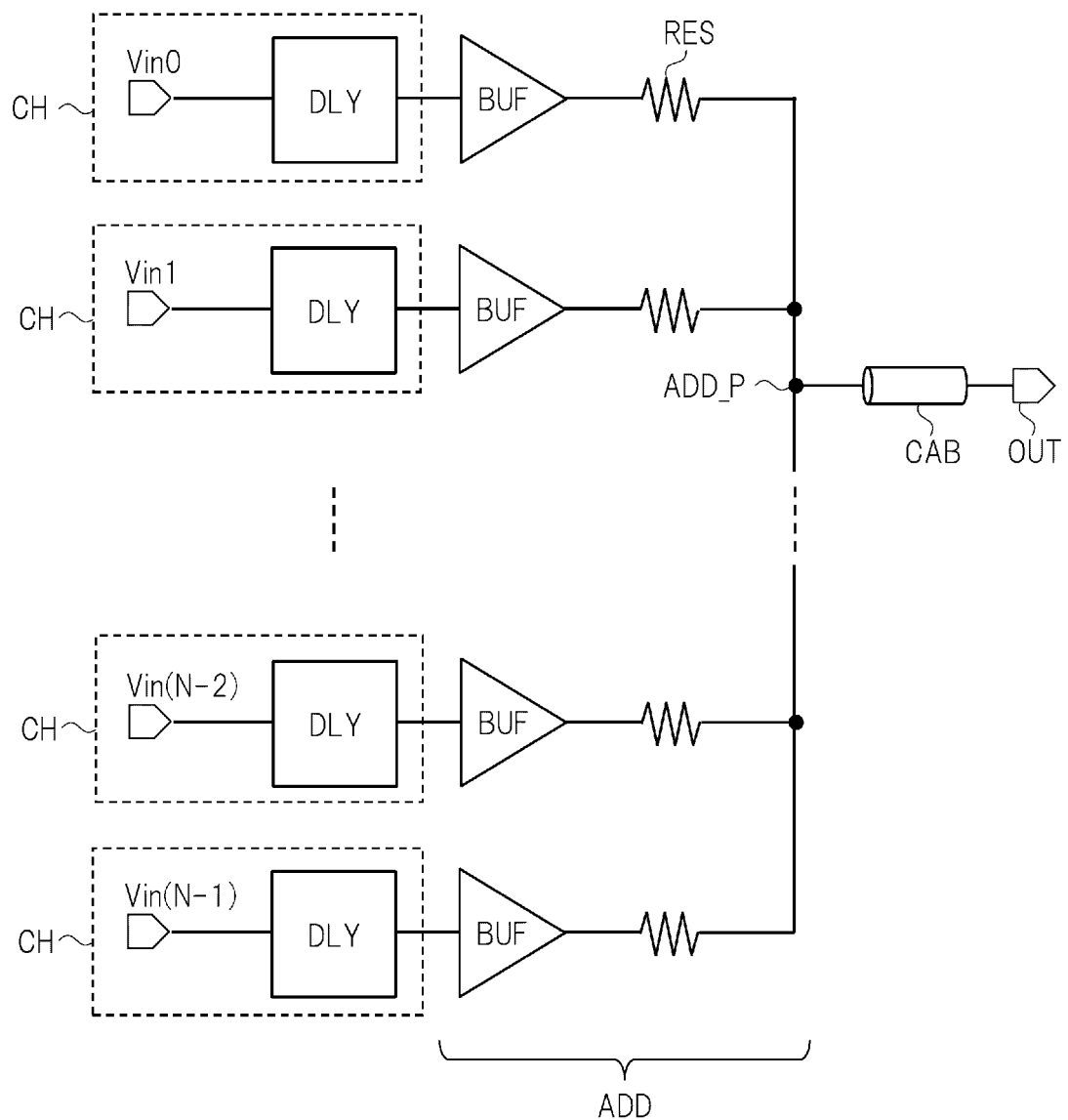
FIG. 3 is a diagram showing an operation of an addition circuit.

Here, first, an operation of the addition circuit will be described by taking a simplified addition circuit as an example. FIG. 3 is a diagram showing the operation of the addition circuit. FIG. 3 shows a configuration of the simplified addition circuit ADD and a connection relationship between the addition circuit ADD and the corresponding transducer channel CH. FIG. 3 shows an example in which the subarray SUB includes N transducer channels CH. Terminals Vin0, . . . , Vin(N−1) of the transducer channels indicate terminals for transmitting the amplified reception signals transmitted from the corresponding low noise amplifiers LNA.

In each transducer channel CH, the amplified reception signal is input to the delay circuit DLY, and a delay is given to the reception signal in the delay circuit DLY. The delayed reception signal is converted into a low impedance reception signal by a corresponding amplifier BUF. The reception signal after impedance conversion is transmitted to an addition point ADD_P via a resistor RES. At the addition point ADD_P, converted reception signals transmitted from all transducer channels CH included in the subarray SUB are added to generate the addition signal. The addition signal is transmitted from the addition output terminal OUT to the corresponding reception channel AFE of the main unit 300 via a cable CAB.

In this way, by coupling output of buffer circuits BUF with the N transducer channels CH via resistors RES, an addition output obtained by interpolation averaging voltages of the resistors RES is obtained as the addition signal at the addition point ADD_P.

By far, the addition of signals (reception signals) is referred to for the sake of convenience. However, addition of a plurality of signals and multiplication by a gain of 1/N is equivalent to averaging. In the signal processing, since there is no large difference between addition and multiplication by a constant gain and multiplication by a constant gain on average, addition including averaging is referred to.

Since the buffer circuit BUF is a component necessary for transmitting the addition signal under a load of the cable CAB, the buffer circuit BUF is explicitly described. An output impedance of the buffer circuit BUF and an impedance when a series impedance of the resistors RES is N in parallel constitute the output impedance of the addition circuit.

Figure 4:
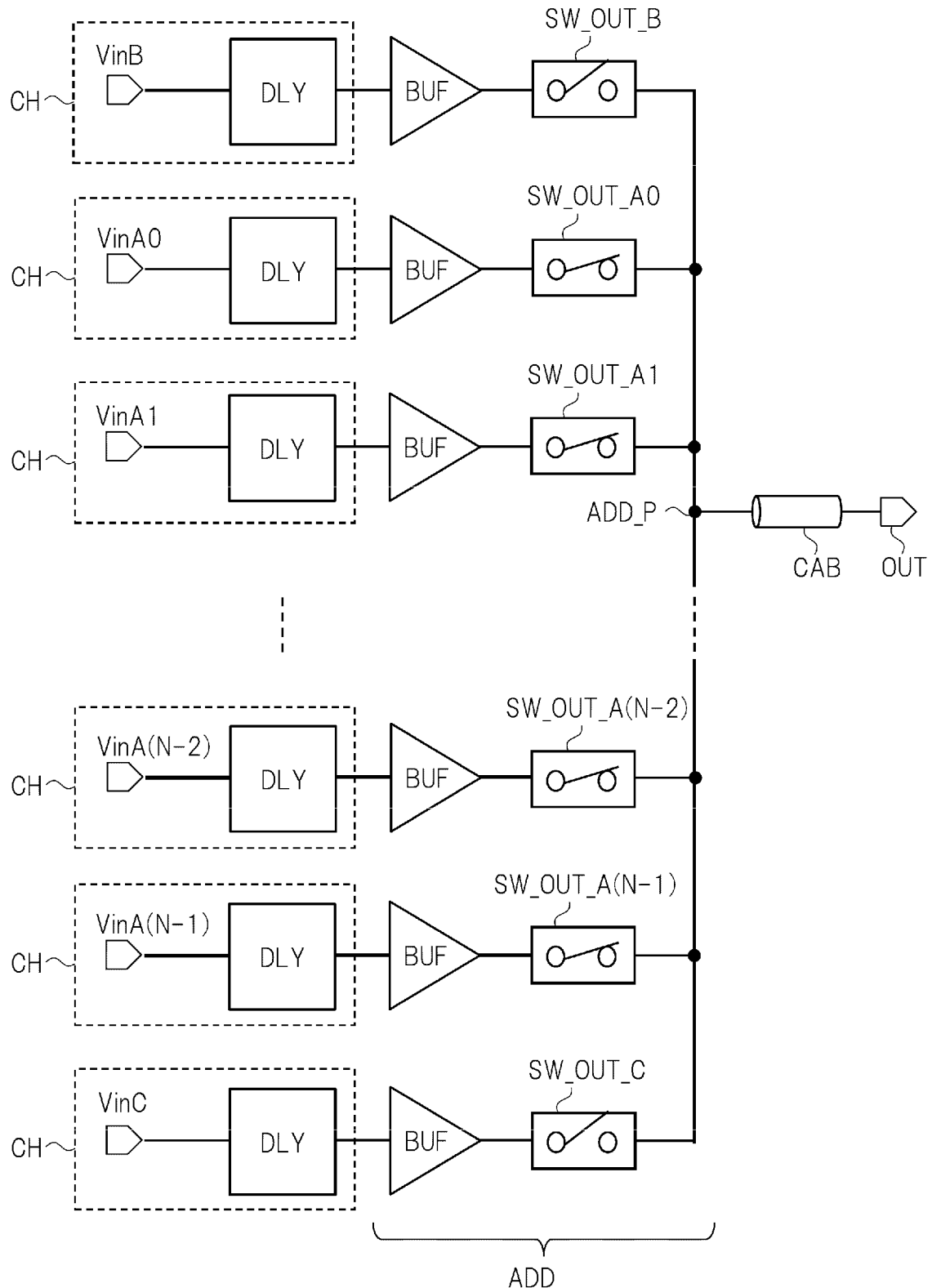
FIG. 4 is a diagram in which a resistor in FIG. 3 is replaced with a switch.

FIG. 4 is a diagram in which the resistor in FIG. 3 is replaced with an output switch. In FIG. 4, in addition to the transducer channels CH in FIG. 3, two transducer channels CH including terminals VinB and VinC are shown together. The added transducer channels CH are for convenience to show a function of the switch. The number of the added transducer channels CH is not limited to the example in FIG. 4.

When the delayed reception signal is transmitted from each transducer channel CH, the delayed reception signal is converted into the low-impedance reception signal by the corresponding buffer circuit BUF. The reception signal after the impedance conversion is transmitted to the addition point ADD_P via the switch.

As shown in FIG. 4, the resistors RES in FIG. 3 are replaced with output switches SW_OUT_A0, ..., SW_OUT_A(N-1). The output switches SW_OUT_A0, ..., SW_OUT_A(N-1) to be turned on have the on-resistance and thus are equivalent to the resistor RES.

On the other hand, as shown in FIG. 4, output switches SW_OUT_B and SW_OUT_C are turned off. Since the switch that is turned off has a resistance value close to infinity, the reception signals transmitted from the terminals VinB and VinC are not transmitted to the addition point ADD_P. Therefore, the transducer channels CH corresponding to the output switches SW_OUT_B and SW_OUT_C do not contribute to the addition of the reception signals. That is, also in FIG. 4, the transducer channels CH including the terminals VinA, ..., VinA(N-1) constitute one subarray SUB.

At the addition point ADD_P, only the reception signals transmitted from the terminals VinA0, ..., VinA(N-1) are added. The addition signal is transmitted to the corresponding reception channel AFE of the main unit 300 via the cable CAB. In this way, by replacing the resistor with the switch, the number of transducer channels for generating the addition signal is appropriately changed. In this way, the transducer channels CH constituting the subarray SUB can be appropriately selected by turning on/off the output switch SW_OUT.

Figure 5:
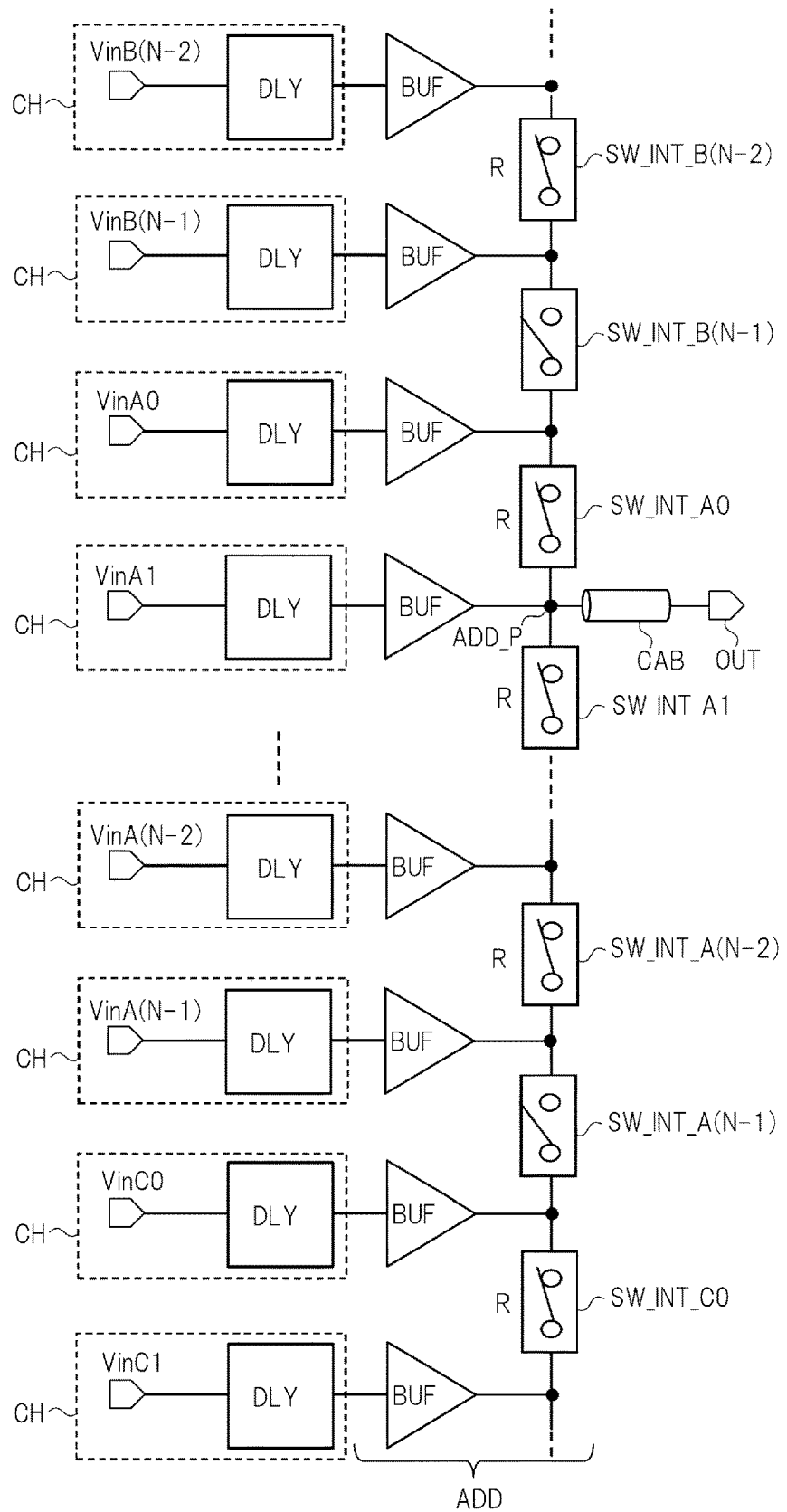
FIG. 5 is a diagram showing a problem of the addition circuit.

Next, problems related to FIGS. 3 and 4 will be described in detail. FIG. 5 is a diagram showing the problems of the addition circuit. FIG. 5 shows the addition circuit in which the buffer circuit BUF is provided on an output side of each transducer channel CH, and the switch is provided between the outputs of adjacent buffer circuits BUF.

As shown in FIG. 5, since inter-output switches SW_INT_B(N-1) and SW_INT_A(N-1) are turned off, only the reception signals transmitted from the terminals VinA0, ... VinA(N-1) are added at the addition point ADD_P.

On the other hand, since the inter-output switch SW_INT_B(N-2) is turned on, the reception signals transmitted from the terminals VinB(N-2) and VinB (N-1) are added as another group. Similarly, since the inter-output switch SW_INT_C0 is turned on, the reception signals transmitted from the terminals VinC0 and VinC1 are added as a group different from these.

However, according to the configuration in FIG. 5, the resistance values between the buffer circuits BUF and the addition point ADD_P (or the addition output terminal OUT) vary among the transducer channels CH depending on the number of switches passing through the addition point ADD_P (or the addition output terminal OUT) and each buffer circuit BUF. Therefore, the addition of the reception signals in FIG. 5 is not a simple interpolation averaging, and the interpolation averaging is weighted. For example, the resistance value from the buffer circuit BUF corresponding to the terminal VinA0 to the addition point ADD_P is the resistance value (R) of one switch. The resistance value from the buffer circuit BUF corresponding to the terminal VinA (N-1) to the addition point ADD_P is the resistance value ((N-2)×R) of N-2 switches arranged in series.

A premise of the resistance interpolation averaging is that the resistance values from the buffer circuits BUF to the addition point ADD_P are equal for all the transducer channels CH in the subarray SUB. However, when the resistance value fluctuates depending on a position at which the addition signal is extracted, the weighted average is obtained, and the gain of the reception signal varies for each transducer channel. Then, the desired addition operation cannot be obtained due to the influence of the on-resistance of the switch.

Figure 6:
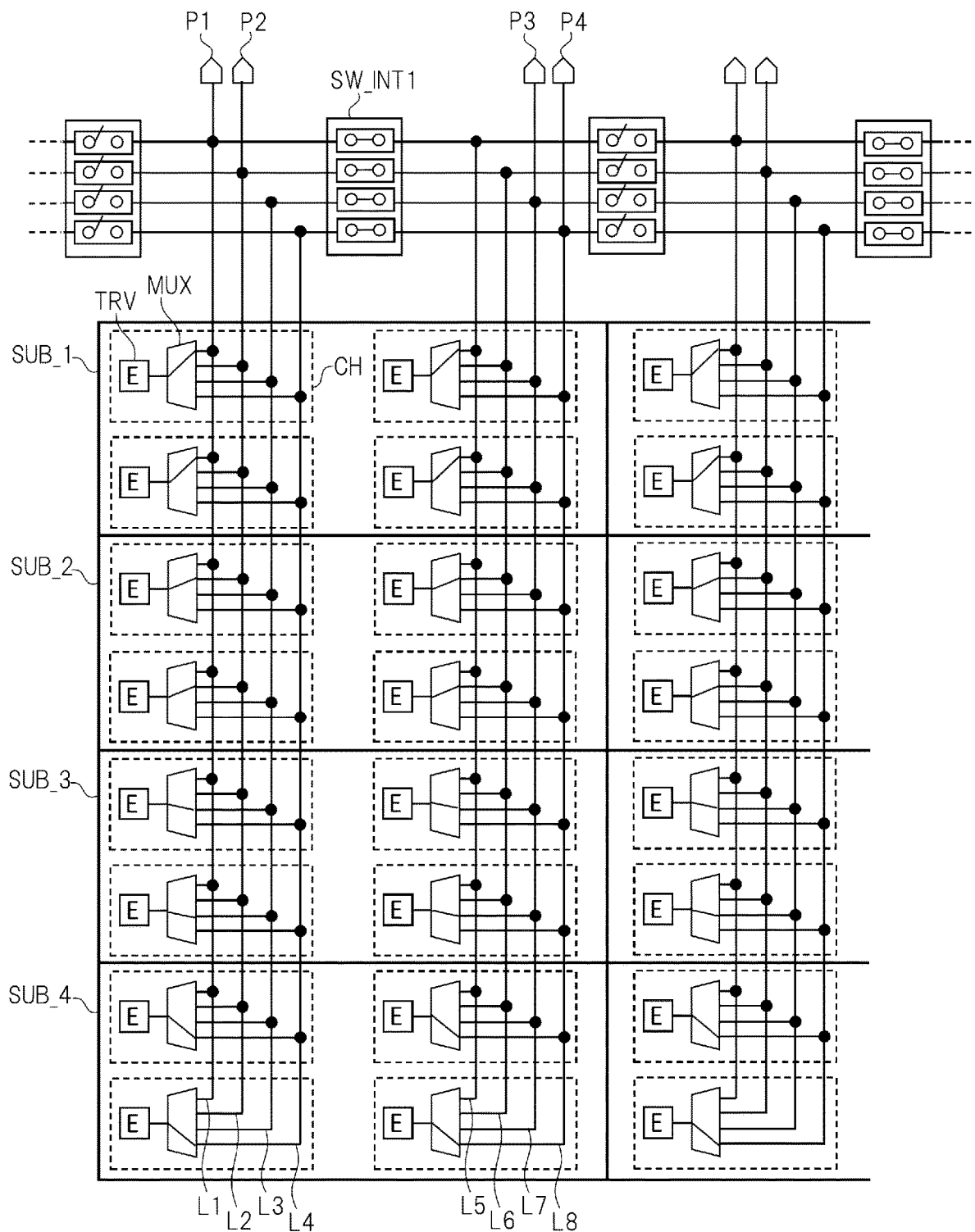
FIG. 6 is a diagram showing a specific circuit configuration for implementing FIG. 5.

FIG. 6 is a diagram showing a specific circuit configuration for implementing FIG. 5. FIG. 6 shows an example in which each subarray includes four (2×2) transducer channels CH. That is, the addition circuit in FIG. 6 adds the reception signals of the four transducer channels to generate the addition signal. In FIG. 6, four subarrays each including 2×2 transducer channels, which are addition units, are vertically arranged. Each of the subarrays SUB has a configuration in which two transducer channel rows each including two transducer channels CH arranged in a vertical direction (first direction) in the drawing are arranged in a horizontal direction (second direction) in the drawing.

Then, corresponding wirings (transducer channel row wirings) are provided for each transducer channel row. For example, wirings L1 to L4 correspond to a left transducer channel row of subarrays SUB1 to SUB4, respectively. Wiring lines L5 to L8 correspond to a right transducer channel row of the subarrays SUB1 to SUB4, respectively.

In the transducer channels CH shown in FIG. 6, a 1:4 multiplexer MUX is provided on an output side of the transmission and reception circuit TRV. Each of the transducer channels CH is coupled to corresponding wirings via the multiplexer MUX. The wirings L1 and L5 are coupled to each other via an inter-output switch SW_INT1. Accordingly, the addition signal of the subarray SUB_1 is transmitted to an addition output terminal (addition point) P1.

Similarly, the addition signal of the subarray SUB_2 is transmitted to an addition output terminal P2 via the wirings L2 and L6 coupled to each other. The addition signal of the subarray SUB_3 is transmitted to an addition output terminal P3 via the wirings L3 and L7 coupled to each other. The addition signal of the subarray SUB_4 is transmitted to an addition output terminal P4 via the wirings L4 and L8 coupled to each other.

However, as shown in FIG. 6, the reception signal output from the left transducer channel row of subarrays SUB passes through the multiplexer MUX only, whereas the reception signal output from the right transducer channel row passes through the multiplexer MUX and the inter-output switch SW_INT1.

That is, in the right transducer channel row, the resistance value between the addition output terminal P1 and the transducer channel CH is larger than that in the left transducer channel row by the on-resistance of the inter-output switch SW_INT1. Therefore, the addition of the signal to the subarray SUB_1 is not a desired resistance interpolation averaging but a weighted averaging, that is, a weighted addition, and the reception signal gain varies among the transducer channels. Such a situation is the same in other subarrays.

Therefore, a configuration in which the resistance value between the addition output terminal (addition point) and each transducer channel of the subarray is the same will be discussed.

Figure 7:
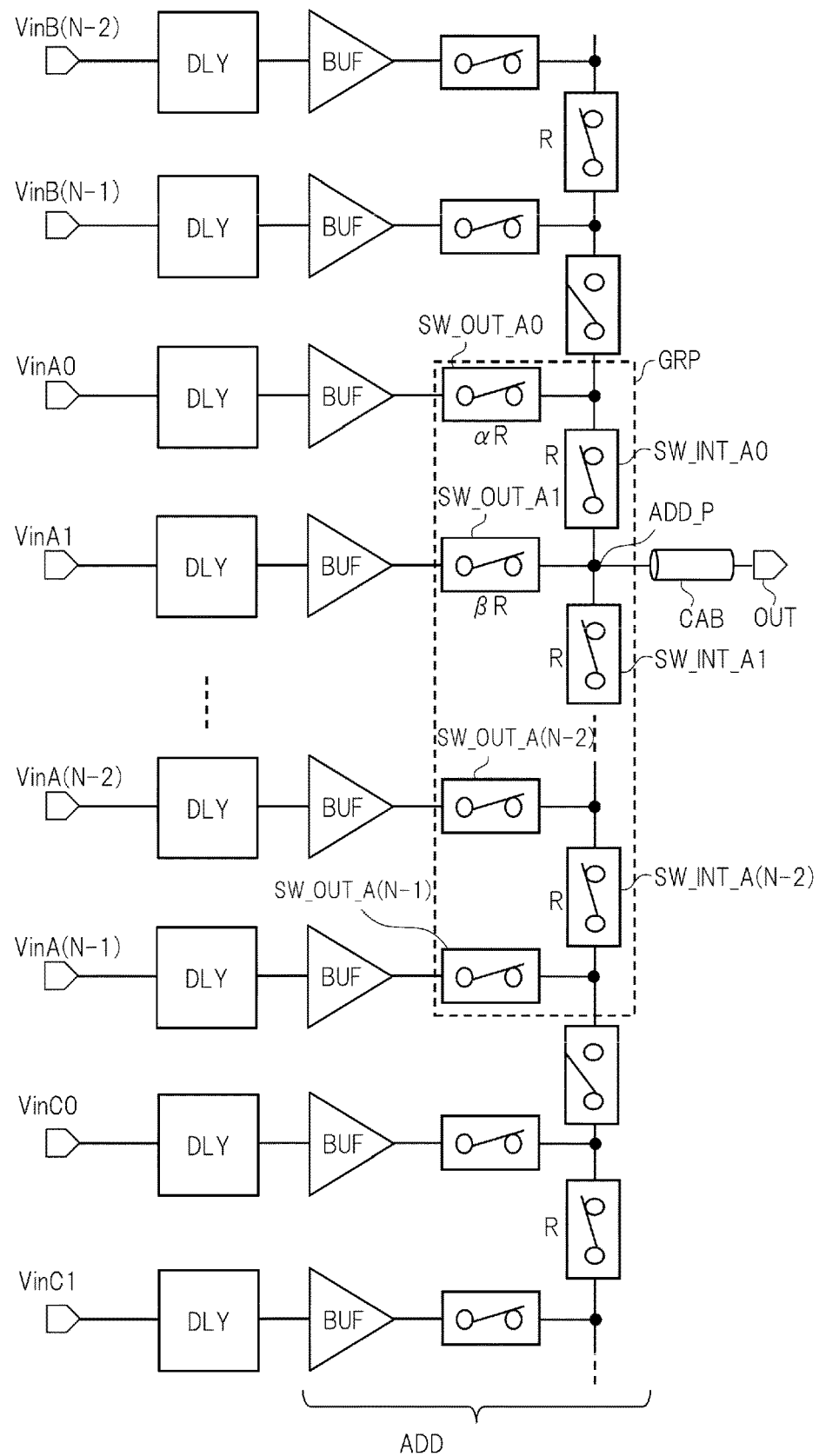
FIG. 7 is a diagram showing an addition circuit for eliminating a variation in a resistance value in association with FIG. 5.

FIG. 7 is a diagram showing an addition circuit for eliminating a variation in the resistance value in association with FIG. 5. In FIG. 7, the buffer circuit BUF that performs the impedance conversion of the reception signal is provided between the delay circuit DLY and the output switch SW_OUT. That is, the output switch SW_OUT is provided on the output side of each transducer channel CH (buffer circuit BUF).

By providing the reception signal output switch SW_OUT, a series-parallel ladder switch including the inter-output switch (second switch) SW_INT and the output switch SW_OUT constitute a switch group GRP between the addition point and the subarray SUB. Then, the switch group GRP or the addition output terminal OUT from the addition point is coupled by the cable CAB.

By appropriately setting the resistance values of the on-resistances of the inter-output switch SW_INT and the output switch SW_OUT, the resistance values between the addition output terminal (addition point) and each transducer channel CH in the subarray SUB are the same. Accordingly, the variation in the reception signal gain among the transducer channels is eliminated.

In FIG. 7, the output switch (first switch) SW_OUT is inserted in series with the output of the buffer circuit BUF. Here, it is assumed that all the on-resistance values of the inter-output switches SW_INT are R. In addition, the on-resistance of the output switch SW_OUT_A0 corresponding to the terminal VinA0 is set to $\alpha R$. The on-resistance of the output switch SW_OUT_A1 corresponding to the terminal VinA1 is set to $\beta R$. A resistance ratio of each output switch SW_OUT is designed such that the reception signal gain does not vary among the transducer channels CH. Accordingly, it is possible to equalize a resistance partial pressure attenuation amount of the reception signals from the transducer channels CH to the addition point ADD_P, and it is possible to equalize reception signal gains from the transducer channels CH to the addition point ADD_P.

In FIG. 7, the addition signal is extracted from between the inter-output switch SW_INT_A0 and the inter-output switch SW_INT_A1, and is transmitted to the reception channel AFE of the main unit 300 via the cable CAB. However, the invention is not limited to such a configuration. Even if the position where the addition signal is extracted is set between other inter-output switches, a combination of resistance ratios of the on-resistances of the output switches SW_OUT can be set so that the reception signal gains from the transducer channels CH are equal.

Figure 8:
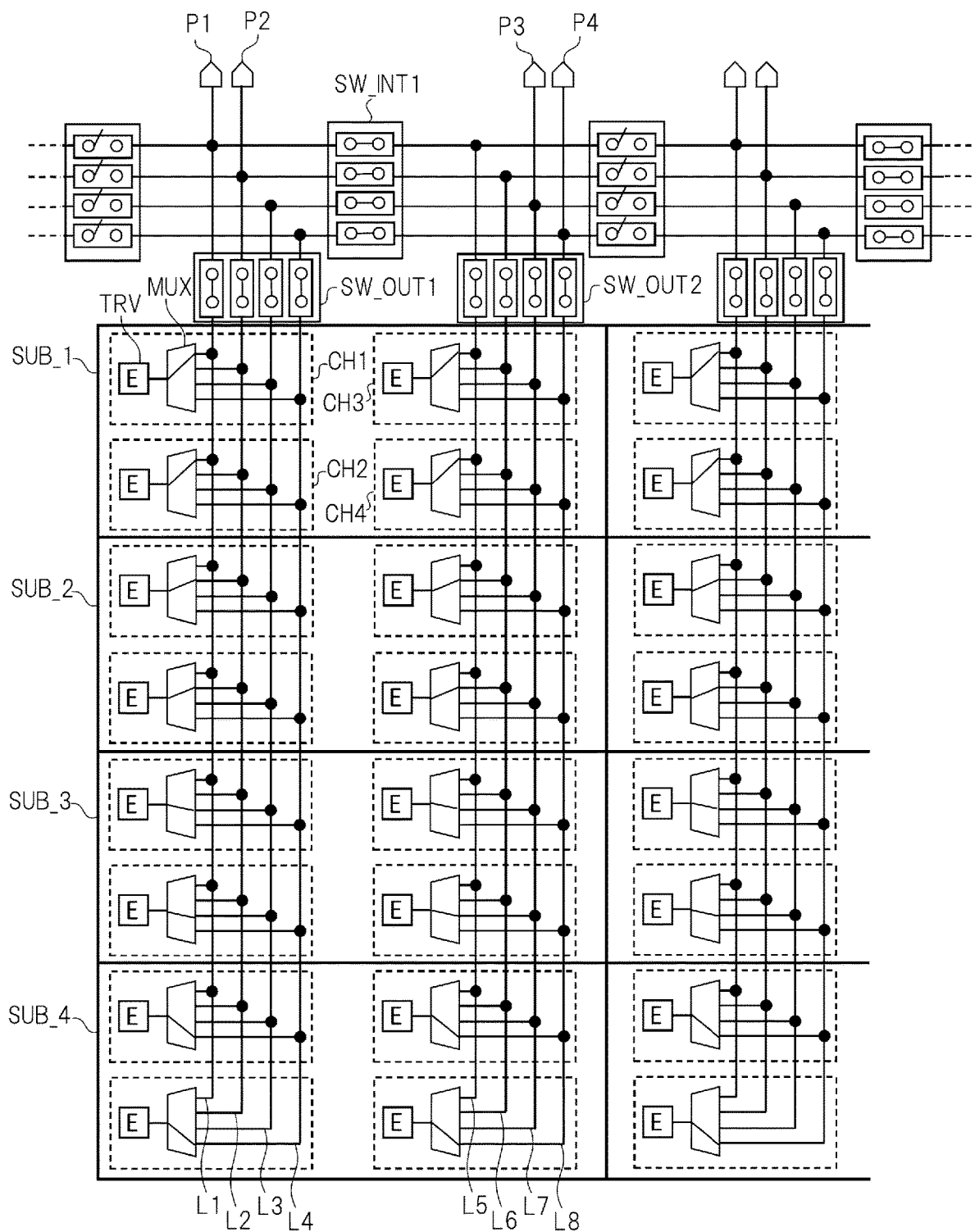
FIG. 8 is a diagram showing a specific circuit configuration for implementing FIG. 7.

FIG. 8 is a diagram showing a specific circuit configuration for implementing FIG. 7. FIG. 8 corresponds to FIG. 6. As shown in FIG. 8, the output switch SW_OUT1 is coupled to the wirings L1 to L4. The output switch SW_OUT2 is coupled to the wirings L5 to L8.

Figure 9:
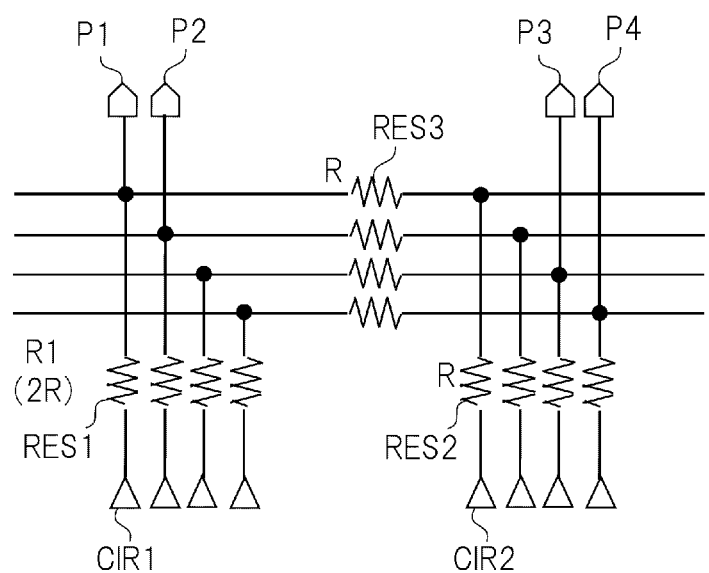
FIG. 9 is a diagram showing an equivalent circuit of FIG. 8.

FIG. 9 is a diagram showing an equivalent circuit of FIG. 8. A circuit CIR1 is a circuit corresponding to a parallel circuit of the transducer channels CH1 and CH2 in FIG. 8. A circuit CIR2 is a circuit corresponding to a parallel circuit of the transducer channels CH3 and CH4 in FIG. 8. For the sake of simplicity, here, the output impedance of the circuits CIR1 and CIR2 is set to $0\Omega$. The resistance value of a resistor RES1 is set to R1. The resistance of a resistor RES2 is set to R. The resistance value of a resistor RES3 is set to R.

In this case, a signal attenuation rate A1 from an output of the circuit CIR1 to the addition output terminal P1 is $A1=2R/(R1+2R)$. A signal attenuation rate A2 from an output of the circuit CIR2 to the addition point ADD_P is $A2=R1/(R1+2R)$. If the signal attenuation rates A1 and A2 are made equal to each other (A1=A2), the signal gains from the transducer channels CH to the addition output terminal P1 can be made equal. Therefore, R1=2R is figured out based on $2R/(R1+2R)=R1/(R1+2R)$. Therefore, by setting R1 to 2R, it is possible to equalize the signal gains from the transducer channels to the addition point ADD_P.

In FIG. 8, by designing the resistance ratio of the on-resistance of each switch between the resistance groups of the output switches SW_OUT1, SW_OUT2, and the inter-output switch SW_INT1 by the above method, it is possible to equalize the signal gains from the transducer channels CH to the addition point even when the addition signal is extracted from any of the addition output terminals P1 to P4.

Figure 10:
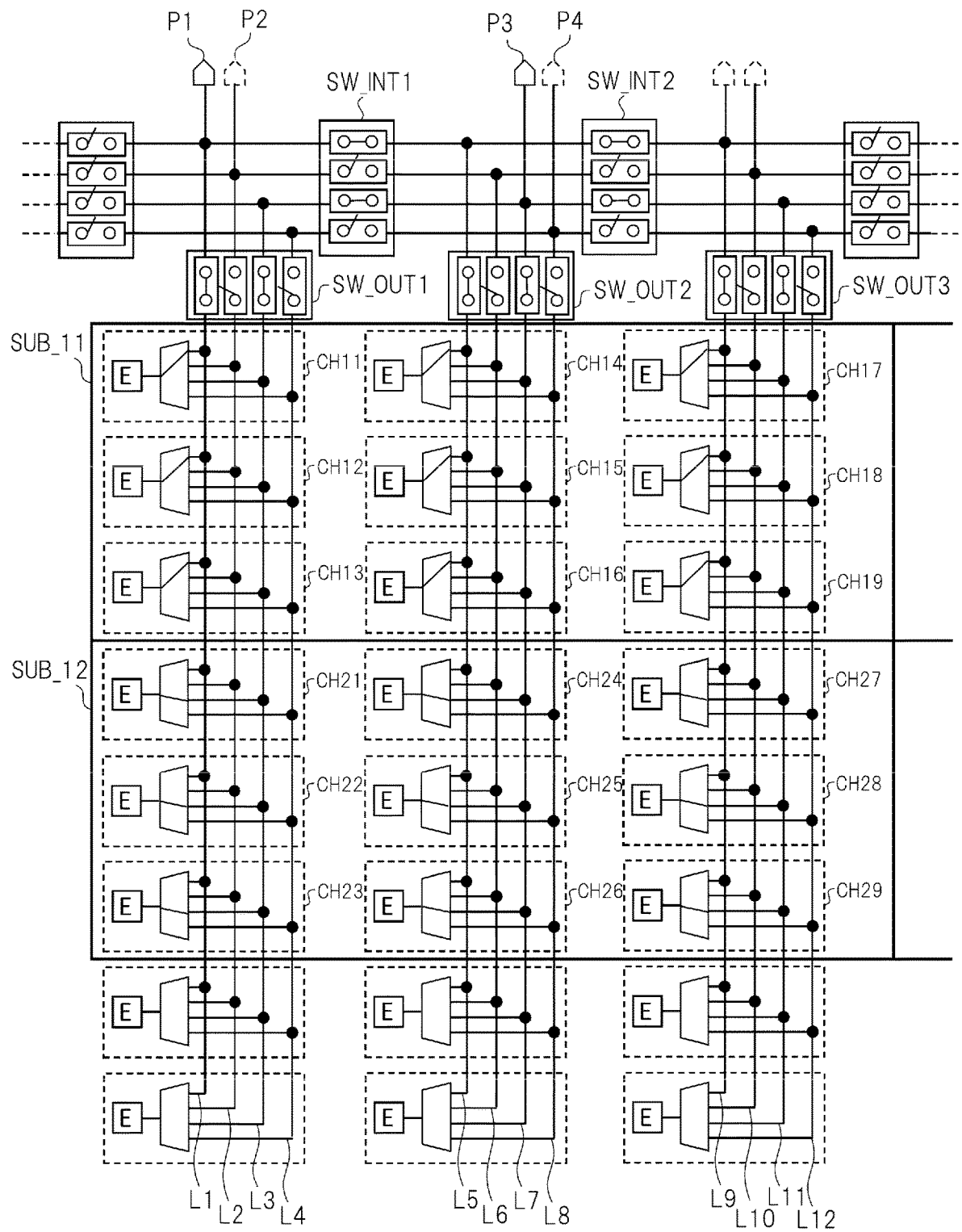
FIG. 10 is a diagram showing a circuit configuration in which the addition unit is switched.

FIGS. 7 to 9 show an example in which the subarray SUB which is the addition unit is constituted by 2×2 transducer channels CH, whereas the addition unit of the transducer channels CH may be switched to another configuration. FIG. 10 is a diagram showing a circuit configuration in which the addition unit is switched. In FIG. 10, the circuit configuration is the same as that of FIG. 8, and the addition unit is switched to 3×3 transducer channels. In FIG. 10, two subarrays SUB_11 and SUB_12 each including nine transducer channels, which are addition units, are vertically arranged. The subarray SUB_11 includes transducer channels CH11 to CH19. The subarray SUB_12 includes transducer channels CH21 to CH29. The reception signals are added for each subarray. The addition signals are transmitted from the two addition output terminals P1 and P3 to the main unit 300.

In the example of FIG. 10, two wirings are used for each transducer channel row. Specifically, in the transducer channel rows including the transducer channels CH11 to CH13 and CH21 to CH23, the wirings L1 and L3 are used. In the transducer channel rows including the transducer channels CH14 to CH16 and CH24 to CH26, the wirings L5 and L7 are used. In the transducer channel rows including the transducer channels CH17 to CH19 and CH27 to CH29, the wirings L9 and L11 are used.

The transducer channels CH11 to CH13 in a left row of the subarray SUB_11 are coupled to the addition point ADD_P only via the output switch SW_OUT1. The transducer channels CH14 to CH16 in a central row are coupled to the addition point ADD_P via the output switch SW_OUT2 and the inter-output switch SW_INT1. The transducer channels CH17 to CH19 in a right row are coupled to the addition output terminal P1 via the output switch SW_OUT3 and the inter-output switches SW_INT2 and SW_INT1. As described above, although the number of stages of switches coupled is different depending on the row, the resistance ratio (or resistance value) of the on-resistance of each output switch may be set to a value figured out based on the signal attenuation rate between the addition output terminal and each transducer channel. The same applies to the subarray SUB_12.

In FIGS. 7, 8, 10, and the like, when the number of the addition output terminals is larger than the number of the reception channel AFEs of the main unit 300, the addition output terminals and the reception channel AFEs may be coupled by the number of the reception channel AFEs. In this case, the two-dimensional array ultrasonic probe 100 may be coupled to a plurality of main unites.

For example, there is a first main unit in which the number of addition output terminals of the two-dimensional array ultrasonic probe 100 is N and the number of reception channel AFEs is M and a second main unit in which the number of reception channel AFEs is L. When N≥M>L, M addition output terminals among the N addition output terminals may be coupled to the first main unit, and L addition output terminals may be coupled to the second main unit.

Further, the L addition output terminals may be a subset of the M addition output terminals. In other words, all addition output terminals coupled to the second main unit may be coupled to the first main unit 1.

Accordingly, coupling between a single 2D array ultrasonic probe and a plurality of main unites is enabled. A wide reception aperture is used regardless of the number of reception channels of the main unit so that a signal-to-noise ratio can be ensured even in a main unit having a small number of reception channels.

FIG. 11 is a diagram showing an equivalent circuit of FIG. 10. A circuit CIR11 corresponds to a parallel circuit of the transducer channels CH11 to CH13 in FIG. 10. A circuit CIR12 corresponds to a parallel circuit of the transducer channels CH21 to CH23 in FIG. 10. A circuit CII13 corresponds to a parallel circuit of the transducer channels CH14 to CH16 in FIG. 10. A circuit CII14 corresponds to a parallel circuit of the transducer channels CH24 to CH26 in FIG. 10. A circuit CIR15 corresponds to a parallel circuit of the transducer channels CH17 to CH19 in FIG. 10. A circuit CIR16 corresponds to a parallel circuit of the transducer channels CH27 to CH29 in FIG. 10.

Again, for simplicity, the output impedance of the circuits CIR11 to CIR16 is set to 0Ω. The resistance value of the resistor RES11 is set to R1. The resistance value of the resistor RES12 is set to R2. The resistance value of the resistor RES13 is set to R3. The resistance value of the resistor RES14 is set to R4. The resistance values of the resistors RES15 to RES16 are set to R. The resistance value of each of the resistors RES21 to RES24 is set to R.

FIG. 12 is a diagram showing a list of formulas of the signal attenuation rate in FIG. 11. At this time, a signal attenuation rate A11 from the output of the circuit CIR11 to the addition output terminal P1 is expressed by Formula 1 in FIG. 12. A signal attenuation rate A13 from the output of the circuit CIR13 to the addition output terminal P1 is expressed by Formula 2 in FIG. 12. A signal attenuation rate A15 from the output of the circuit CIR15 to the addition output terminal P1 is expressed by Formula 3 in FIG. 12.

On the other hand, a signal attenuation factor A12 from the output of the circuit CIR12 to the addition output terminal P3 is expressed by Formula 4 in FIG. 12. A signal attenuation rate A14 from the output of the circuit CIR14 to the addition output terminal P3 is expressed by Formula 5 in FIG. 12. A signal attenuation rate A16 from the output of the circuit CIR16 to the addition output terminal P3 is expressed by Formula 4 in FIG. 12.

In order for the signal gains from each transducer channel to the addition output terminals P1 and P3 to be equal, all signal attenuation rates A11 to A16 need to be equal. Accordingly, the resistance ratio of the on-resistance of each switch between the switches is calculated. Further, the resistance value of each switch is figured out to be R1=4R, R3=2R, R2=R, and R4=2R.

If the on-resistance of each switch is designed by the resistance ratio based on these values, it is possible to equalize the signal gain from each transducer channel to the addition point between the subarrays SUB_11 and SUB_12 having different addition units.

Incidentally, in the same circuit configuration, it is necessary to switch the resistance value of the on-resistance of each switch in accordance with the switching of the addition unit. Therefore, a method for switching the on-resistance will be described below.

Figure 13:
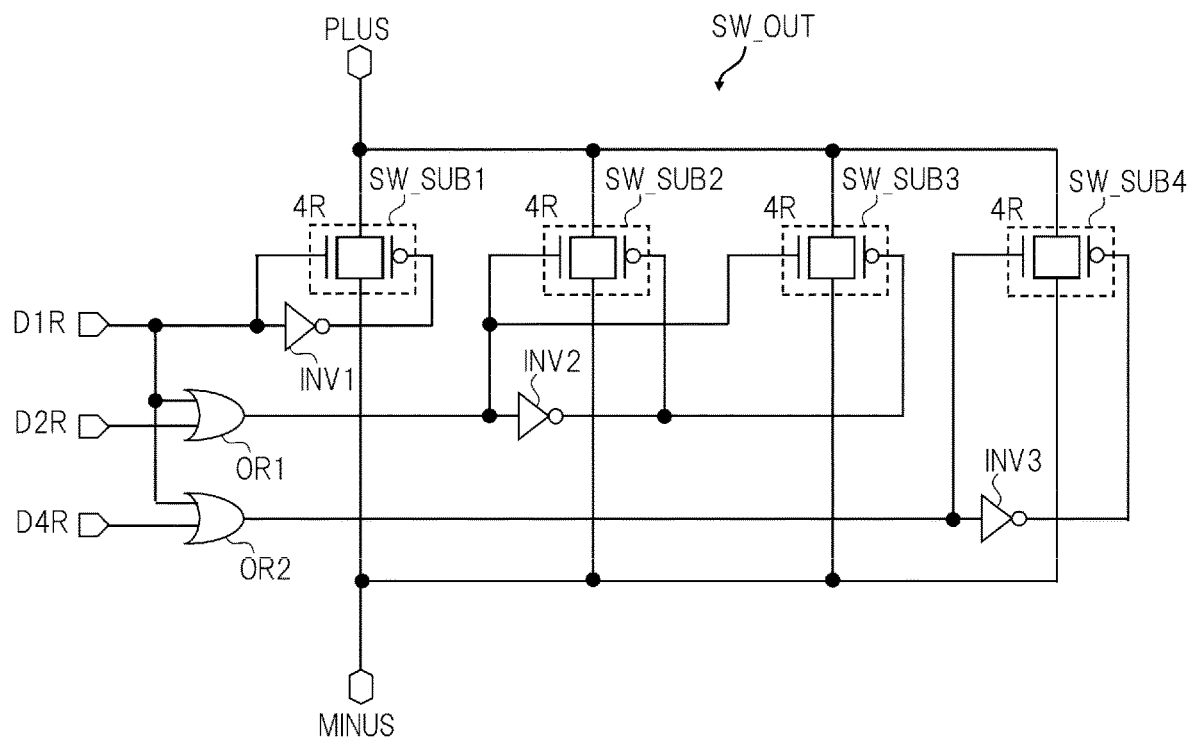
FIG. 13 is a diagram showing a method for switching an on-resistance of the switch.

FIG. 13 is a diagram showing a method for switching the on-resistance of the switch. FIG. 13 shows the configuration of the output switch SW_OUT coupled to one wiring. In the output switch SW_OUT in FIG. 13, four subswitches SW_OUT SUB1 to SW_OUT SUB4 having the same (for example, 4R) resistance value of the on-resistance are coupled in parallel. Each of the subswitches SW_OUT SUB1 to SW_OUT SUB4 includes an NMOSFET (hereinafter, referred to as an NMOS) and a PMOSFET (hereinafter, referred to as a PMOS) coupled in parallel.

A resistance value setting signal D1R is supplied to a gate of the NMOS of the subswitch SW_OUT SUB1. An inverted signal of the resistance value setting signal D1R is supplied to a gate of the PMOS of the subswitch SW_OUT SUB1.

An output signal of an OR circuit OR1 is supplied to a gate of the NMOS of the subswitch SW_OUT SUB2. An inverted signal of the output signal of the OR circuit OR1 is supplied to a gate of the PMOS of the subswitch SW_OUT SUB2.

The output signal of the OR circuit OR1 is supplied to a gate of the NMOS of the subswitch SW_OUT SUB3. The inverted signal of the output signal of the OR circuit OR1 is supplied to a gate of the PMOS of the subswitch SW_OUT SUB3.

An output signal of the OR circuit OR2 is supplied to a gate of the NMOS of the subswitch SW_OUT SUB4. An inverted signal of the output signal of the OR circuit OR2 is supplied to a gate of the PMOS of the subswitch SW_OUT SUB4.

Resistance value setting signals D1R and D2R are input to the OR circuit OR1. Resistance value setting signals D1R and D4R are input to the OR circuit OR2.

In the configuration of FIG. 13, the resistance value of the output switch SW_OUT can be switched in three stages. For example, when a logic level of the resistance value setting signal D1R is high, the subswitches SW_OUT SUB1 to SW_OUT SUB4 are turned on. In this case, the on-resistance value of the output switch SW_OUT is R. Next, when the logic level of the resistance value setting signal D2R is high and the logic level of the resistance value setting signals D1R and D4R is low, only the subswitches SW_OUT SUB2 and SW_OUT SUB3 are turned on. In this case, the on-resistance value of the output switch SW_OUT is 2R. Next, when the logic level of the resistance value setting signal D4R is high and the logic level of the resistance value setting signals D1R and D2R is low, only the subswitch SW_OUT SUB4 is turned on. In this case, the on-resistance value of the output switch SW_OUT is 4R.

In this way, a desired on-resistance value of the output switch SW_OUT is set by the subswitch to be turned on. The on-resistance of the MOS varies depending on a fluctuation of a threshold voltage, a fluctuation of a power supply voltage, and a temperature. However, as shown in FIGS. 9 and 11, accuracy of the resistance ratio is necessary to equalize the reception signal gains from the transducer channels to the addition point. In IC design, it is difficult to obtain the resistance value of the on-resistance of each MOS with high accuracy. However, it is possible to increase the accuracy of the resistance ratio between the switches by the number of MOSs to be arranged in parallel or a ratio of a channel width of each MOS. Therefore, the configuration in FIG. 13 is suitable for installation as an IC.

In the output switch of FIG. 13, the NMOS and the PMOS are coupled in parallel and the fluctuation of the on-resistance is small with respect to the fluctuation of a DC level of the signal to be passed. As the DC level decreases, the on-resistance of the NMOS decreases and the on-resistance of the MOSFET increases. On the other hand, as the DC level increases, the on-resistance of the NMOS increases and the on-resistance of the MOSFET decreases.

By arranging the NMOS and the PMOS in parallel in this way, the increase and decrease in the parallel resistance are offset to some extent. However, when the DC level of the signal to be passed is closer to a ground level than that of a power supply, it is not necessary to arrange the subswitch in parallel with the NMOS and the PMOS. In such a case, the output switch may have another configuration.

Figure 14:
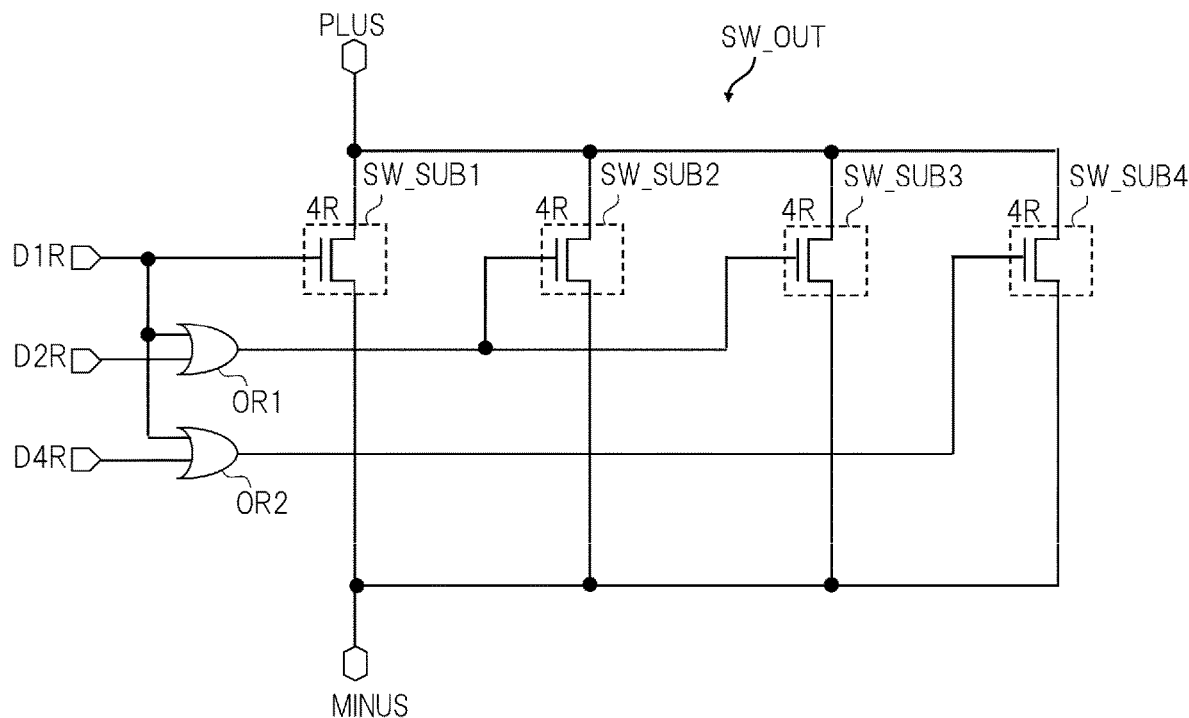
FIG. 14 is a diagram showing a configuration of an output switch different from that of FIG. 13.

FIG. 14 is a diagram showing a configuration of an output switch different from that of FIG. 13. In FIG. 14, the subswitches SW_OUT SUB1 to SW_OUT SUB4 are constituted only by the NMOSs. According to this configuration, a circuit area of the output switch can be reduced.

When the DC level of the signal to be passed is close to that of the power supply, it is possible to constitute the subswitch with the MOSFET only. However, when the same level of gate-source voltage is applied to the MOSFET and NMOS of the same element size, the NMOS has lower on-resistance than the MOSFET. Therefore, it is more advantageous to use the NMOS in order to reduce the noise of the circuit and the output impedance of the IC to increase a driving force.

<Main Effects of Present Embodiment>

According to the present embodiment, a switch group having a ladder structure including the output switch SW_OUT and the inter-output switch SW_INT is constituted between the addition output terminal and the transducer channels CH.

According to this configuration, it is possible to reduce the number of switches and the number of wirings in the IC mounted on the 2D array ultrasonic probe 100. Accordingly, it is possible to switch the addition unit of the reception signal according to the reception channel of the main unit while preventing an increase in the chip area.

Further, according to the present embodiment, the resistance ratio of the on-resistance between each output switch SW_OUT and each inter-output switch SW_INT is set such that the signal attenuation rate between the addition output terminal and each transducer channel CH is equal. According to this configuration, it is possible to prevent the variation in the gain of the reception signal between the addition output terminal and each transducer channel CH. Regardless of a physical position of the transducer channel CH, the gain of the reception signal can be made equal among all transducer channels, and it is possible to prevent generation of a virtual image due to the dependence of the signal gain on the transducer channel.

Further, according to the present embodiment, the output switch SW_OUT and the inter-output switch SW_INT are provided between the delay circuit DLY and the addition output terminals P1 to P4 (OUT). According to this configuration, the influence of ON/OFF control of the output switch SW_OUT and the inter-output switch SW_INT on the reception signal after the delay processing is reduced.

Further, according to the present embodiment, the output switch SW_OUT can switch the on-resistance in accordance with the switching of the addition unit. Specifically, in the output switch SW_OUT, a plurality of subswitches (for example, SW_SUB1 to SW_SUB4) constituted by the MOSFET are coupled in parallel, and the on-resistance is switched by the subswitch to be turned on. According to this configuration, it is possible to cope with a plurality of types of main unites and improve versatility.

Further, according to the present embodiment, the buffer circuit BUF that performs the impedance conversion of the reception signal is provided between each delay circuit DLY and the output switch. According to this configuration, the impedance in an output path of the reception signal can be reduced, and the signal-to-noise ratio can be improved.

Second Embodiment

Next, a second embodiment will be described. A test AC signal may be input to each transducer channel. It is desired to test whether the transducer channel operates as expected from the input to the output of the signal in each transducer channel. An IC tester that tests an IC on a silicon wafer has a plurality of reception channels. The IC can be tested by transmitting a signal from the IC to the plurality of reception channels.

However, most of the reception channels of the IC tester are reception channels for digital signals, and have only a function of determining whether the logic level is high level or low level. The reality is that the IC tester has few reception channels for analog signals that can sample the analog signals and perform analog/digital conversion. Therefore, a test is desired in which a signal of any transducer channel is coupled to an analog reception channel of a tester, and a magnitude of amplitude of the reception signal can be determined as an analog value.

Figure 15:
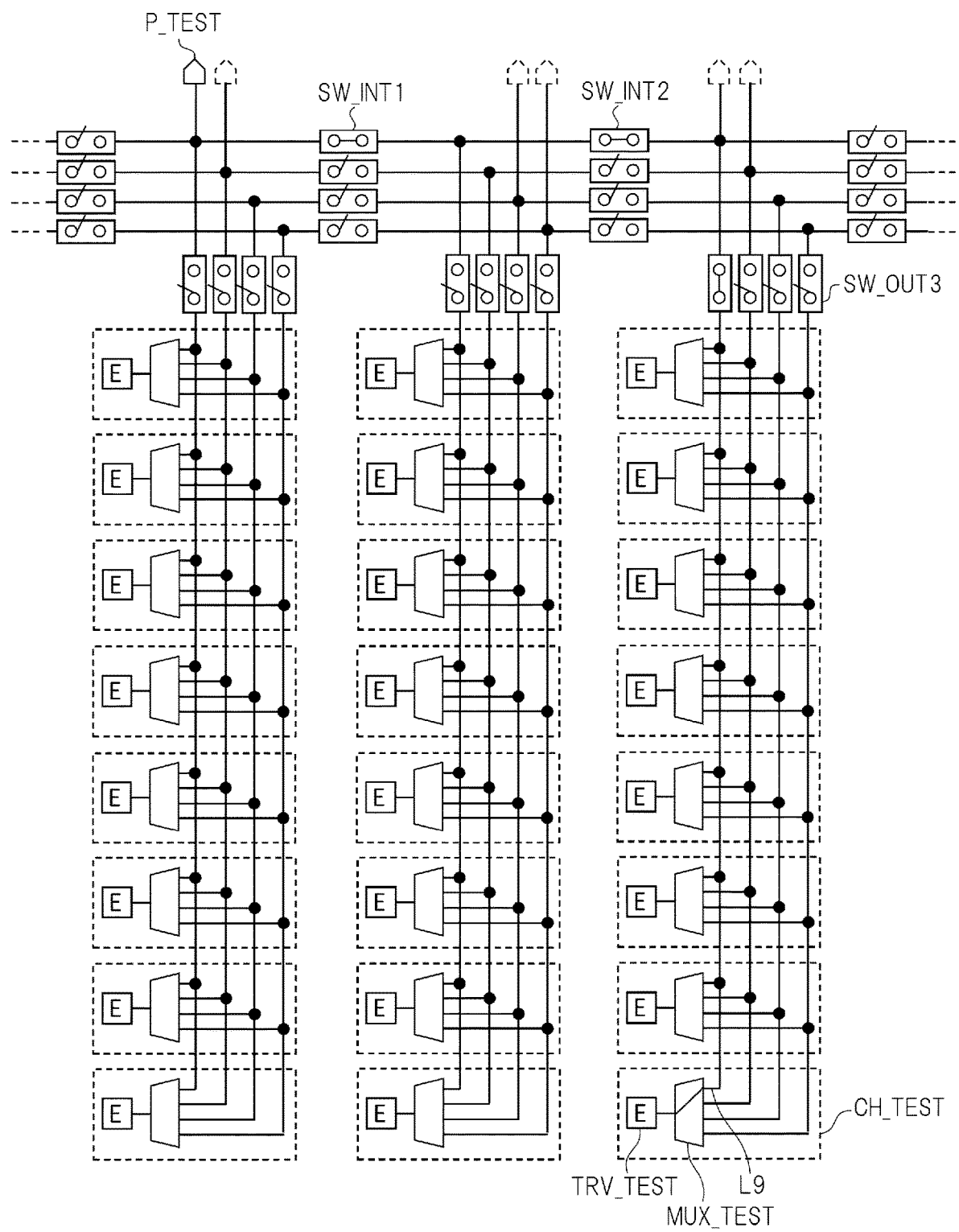
FIG. 15 is a diagram showing a circuit test method according to a second embodiment of the invention.
Figure 16:
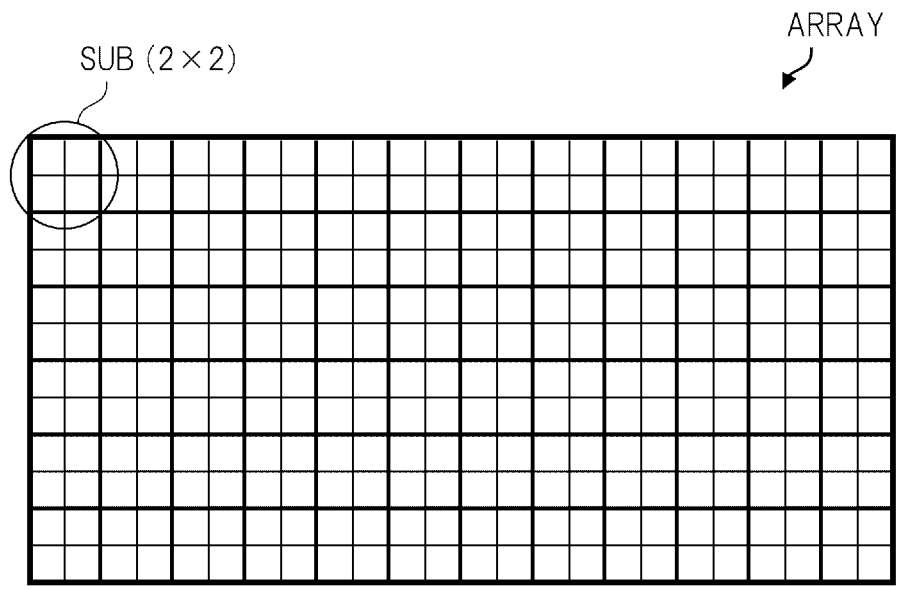
FIG. 16 is a diagram showing an example of a method for adding a reception signal in a two-dimensional transducer array.

FIG. 15 is a diagram showing a circuit test method according to the second embodiment of the invention. FIG. 15 shows an example of routing a transmission and reception circuit TRV_TEST included in a lower right transducer channel CH_TEST to an output terminal P_TEST coupled to the analog reception channel of the IC tester.

In FIG. 15, the transducer channel CH_TEST is coupled to the wiring L9 by a multiplexer MUX_TEST. Then, when the output switch SW_OUT3 and the inter-output switches SW_INT2 and SW_INT1 are turned on, the transducer channel CH_TEST is coupled to the analog reception channel AFE_TEST via the wiring L9 and the like. In other words, the output switch SW_OUT3 and the inter-output switches SW_INT2 and SW_INT1 on a path coupling the addition output terminal P_TEST and the specific transducer channel CH_TEST are turned on.

Accordingly, it is possible to determine the magnitude of the amplitude of the analog reception signal transmitted from the transducer channel CH_TEST and conduction of each switch from the IC tester.

At this time, it is desirable that each switch which is not related to a signal path for testing is turned off. Accordingly, a circuit load at the time of performing the test is reduced, and it is possible to easily perform a conduction test for each transducer channel while switching the switch.

The invention is not limited to the embodiments described above and includes various modifications. Further, a part of the configuration of one embodiment can be replaced with the configuration of another embodiment, and the configuration of another embodiment can be added to the configuration of the one embodiment. A part of the configuration of each embodiment may be added, deleted, or replaced with another configuration. Each member and the relative size described in the drawings are simplified and idealized in order to easily understand the invention, and are more complicated in terms of implementation.

What is claimed is:

1. A two-dimensional array ultrasonic probe in which a plurality of transducer channels are arranged in a first direction and a second direction, each of the plurality of transducer channels including an ultrasonic transducer and a reception circuit that transmits a reception signal of the ultrasonic transducer, the plurality of transducer channels being divided into a plurality of subarrays on a basis of an addition unit of the reception signal, the two-dimensional array ultrasonic probe comprising:
an addition circuit that generates an addition signal by adding reception signals of the transducer channels included in the subarrays on a subarray basis, wherein the addition circuit includes,
between an addition output terminal that outputs the addition signal and the transducer channels, a transducer channel row wiring provided for each transducer channel row including the transducer channels arranged in the first direction on a subarray basis and coupled to the transducer channels of a corresponding transducer channel row, a first switch provided for each transducer channel row wiring and coupled to the corresponding transducer channel row wiring, and a second switch that couples transducer channel row wirings corresponding to transducer channel rows adjacent in the second direction via the first switch.

2. The two-dimensional array ultrasonic probe according to claim 1, wherein a resistance ratio of an on-resistance between each first switch and each second switch is set so that a gain between each transducer channel and the addition output terminal is equal.

3. The two-dimensional array ultrasonic probe according to claim 1, further comprising:

a delay circuit that performs phasing of the reception signals among the plurality of transducer channels on a transducer channel basis; wherein the first switch and the second switch are provided between the delay circuit and the addition output terminal.

4. The two-dimensional array ultrasonic probe according to claim 1, wherein the first switch switches an on-resistance in accordance with switching of the addition unit.

5. The two-dimensional array ultrasonic probe according to claim 4, wherein in the first switch, a plurality of subswitches constituted by MOSFETs are coupled in parallel, and the on-resistance is switched by a subswitch to be turned on.

6. The two-dimensional array ultrasonic probe according to claim 1, further comprising:

a delay circuit that performs phasing of the reception signals among the plurality of transducer channels on a transducer channel basis; and a buffer circuit that performs impedance conversion of the reception signal between each delay circuit and the first switch.

7. The two-dimensional array ultrasonic probe according to claim 1, wherein the first switch and the second switch on a path coupling the addition output terminal and a specific transducer channel are turned on.

8. The addition circuit according to claim 1, further comprising:

a delay circuit that is provided for each transducer channel and performs phasing of the reception signal among the plurality of transducer channels; and a buffer circuit that performs impedance conversion of the reception signal between the buffer circuit and the first switch.

9. The two-dimensional array ultrasonic probe according to claim 1, wherein the first and second switches are both disposed outside of a two-dimensional transducer channel array comprising the plurality of transducer channels.

10. An addition circuit in a two-dimensional array ultrasonic probe in which a plurality of transducer channels are arranged in a first direction and a second direction, each of the plurality of transducer channels including an ultrasonic transducer and a reception circuit that transmits a reception signal of the ultrasonic transducer, the plurality of transducer channels being divided into a plurality of subarrays on a basis of an addition unit of the reception signal, the addition circuit configured to generate an addition signal by adding reception signals of the transducer channels included in the subarrays on a subarray basis, the addition circuit comprising:

between an addition output terminal that outputs the addition signal and the transducer channels, a transducer channel row wiring provided for each transducer channel row including the transducer channels arranged in the first direction on a subarray basis and coupled to the transducer channels of a corresponding transducer channel row;

a first switch provided for each transducer channel row wiring and coupled to the corresponding transducer channel row wiring; and a second switch that couples transducer channel row wirings corresponding to transducer channel rows adjacent in the second direction via the first switch.

11. The addition circuit according to claim 10, wherein a resistance ratio of an on-resistance between each first switch and each second switch is set so that a gain between each transducer channel and the addition output terminal is equal.

12. The addition circuit according to claim 10, wherein the first switch and the second switch are provided between the addition output terminal and a delay circuit that is provided for each transducer channel and performs phasing of the reception signal among the plurality of transducer channels.

13. The addition circuit according to claim 10, wherein the first switch switches an on-resistance in accordance with switching of the addition unit.

14. The addition circuit according to claim 13, wherein in the first switch, a plurality of subswitches constituted by MOSFETs are coupled in parallel, and the on-resistance is switched by a subswitch to be turned on.

15. The addition circuit according to claim 10, wherein the first switch and the second switch on a path coupling the addition output terminal and a specific transducer channel are turned on.

16. The addition circuit according to claim 10, wherein the first and second switches are both disposed outside of a two-dimensional transducer channel array comprising the plurality of transducer channels.

* * * * *